US010492817B2

(12) United States Patent
Mirza et al.

(10) Patent No.: US 10,492,817 B2
(45) Date of Patent: Dec. 3, 2019

(54) ENDOSCOPIC SURGICAL BLADE AND USE THEREOF

(75) Inventors: Ather Mirza, Smithtown, NY (US); Romi Mirza, Smithtown, NY (US)

(73) Assignee: A.M. SURGICAL, INC., Smithtown, NY (US)

( * ) Notice: Subject to any disclaimer, the term of this patent is extended or adjusted under 35 U.S.C. 154(b) by 839 days.

(21) Appl. No.: 13/006,077

(22) Filed: Jan. 13, 2011

(65) Prior Publication Data

US 2011/0130779 A1  Jun. 2, 2011
US 2012/0296357 A2  Nov. 22, 2012

Related U.S. Application Data

(63) Continuation-in-part of application No. 12/716,640, filed on Mar. 3, 2010, now Pat. No. 8,827,893, which is a continuation-in-part of application No. 12/400,485, filed on Mar. 9, 2009, now Pat. No. 8,821,383.

(51) Int. Cl.
| | | |
|---|---|---|
| *A61B 1/04* | (2006.01) | |
| *A61B 17/32* | (2006.01) | |
| *A61B 17/34* | (2006.01) | |
| *A61B 1/018* | (2006.01) | |
| *A61B 17/00* | (2006.01) | |
| *A61B 17/16* | (2006.01) | |
| *A61B 90/00* | (2016.01) | |

(52) U.S. Cl.
CPC ...... *A61B 17/320036* (2013.01); *A61B 1/018* (2013.01); *A61B 17/3421* (2013.01); *A61B 17/1659* (2013.01); *A61B 90/361* (2016.02); *A61B 2017/00907* (2013.01); *A61B 2090/062* (2016.02)

(58) Field of Classification Search
USPC .......................................... 606/79, 167, 170
See application file for complete search history.

(56) References Cited

U.S. PATENT DOCUMENTS

| | | | | |
|---|---|---|---|---|
| 1,448,305 | A * | 3/1923 | Langbein ........... | A61B 17/3213 30/339 |
| 1,500,402 | A * | 7/1924 | Lewis ....................... | B26B 5/00 279/105.1 |
| 1,888,489 | A * | 11/1932 | Brown ............... | A61B 17/3213 279/44 |

(Continued)

OTHER PUBLICATIONS

Notification of Transmittal of the International Search Report and the Written Opinion of the International Searching Authority, Application No. PCT/US2010/026157, Form PCT/ISA/220 (dated Jul. 2010).

(Continued)

*Primary Examiner* — Matthew J Kasztejna
(74) *Attorney, Agent, or Firm* — Ping Wang; Morris, Manning & Martin, LLP

(57) ABSTRACT

An endoscopic surgical blade is disclosed. The blade is part of an endoscopic knife assembly which also has a knife tube and alignment ring. The endoscopic knife assembly is for use in endoscopic surgery by insertion of the assembly though a slotted cannula. The knife tube is hollow and allows the insertion of an endoscope for viewing of the surgical procedure. The blade has an upper and a lower cutting surface on the forward edge, which meet at an angle at a crotch.

8 Claims, 21 Drawing Sheets

(56) References Cited

U.S. PATENT DOCUMENTS

| | | | | |
|---|---|---|---|---|
| 3,610,246 | A * | 10/1971 | Salmon | A61B 17/3213 30/294 |
| 3,967,377 | A * | 7/1976 | Wells | 30/320 |
| 3,990,451 | A * | 11/1976 | Gibbs | 606/174 |
| 4,011,657 | A * | 3/1977 | Vance | B26B 5/00 279/77 |
| 4,081,907 | A * | 4/1978 | Bosshold | B43M 7/002 30/294 |
| 4,850,354 | A * | 7/1989 | McGurk-Burleson et al. | 606/170 |
| 5,029,573 | A * | 7/1991 | Chow | 600/104 |
| 5,272,812 | A * | 12/1993 | Doucette | B26B 5/00 30/330 |
| 5,295,974 | A | 3/1994 | O'Laughlin | |
| 5,323,765 | A * | 6/1994 | Brown | A61B 17/320036 128/898 |
| 5,366,465 | A | 11/1994 | Mirza | |
| 5,397,333 | A * | 3/1995 | Knoepfler | 606/170 |
| 5,412,871 | A * | 5/1995 | Reyburn | B26B 27/005 30/2 |
| 5,413,580 | A * | 5/1995 | Stephenson | 606/170 |
| 5,507,800 | A * | 4/1996 | Strickland | 606/167 |
| 5,578,051 | A | 11/1996 | Mirza | |
| 5,620,446 | A * | 4/1997 | McNamara | A61B 17/320036 128/898 |
| 5,649,946 | A * | 7/1997 | Bramlet | A61B 17/320036 606/159 |
| 5,827,311 | A * | 10/1998 | Berelsman et al. | 606/167 |
| 5,957,944 | A * | 9/1999 | Khuri et al. | 606/170 |
| 5,968,061 | A | 10/1999 | Mirza | |
| 5,984,941 | A * | 11/1999 | Wilson | A61B 17/3496 604/256 |
| 6,428,503 | B1 * | 8/2002 | Kierce | 604/43 |
| 7,041,115 | B2 | 5/2006 | Mirza et al. | |
| 8,813,372 | B2 * | 8/2014 | Scott | B23D 51/10 279/24 |
| 2002/0019611 | A1 | 2/2002 | Green | |
| 2002/0026195 | A1 * | 2/2002 | Layne | A61B 17/3417 606/92 |
| 2002/0123724 | A1 | 9/2002 | Douglas et al. | |
| 2005/0137528 | A1 | 6/2005 | Wilkinson | |
| 2007/0288043 | A1 | 12/2007 | Rehnke | |

OTHER PUBLICATIONS

International Search Report and the Written Opinion of the International Searching Authority of International Application No. PCT/US2011/064636, dated Jun. 14, 2012.

* cited by examiner

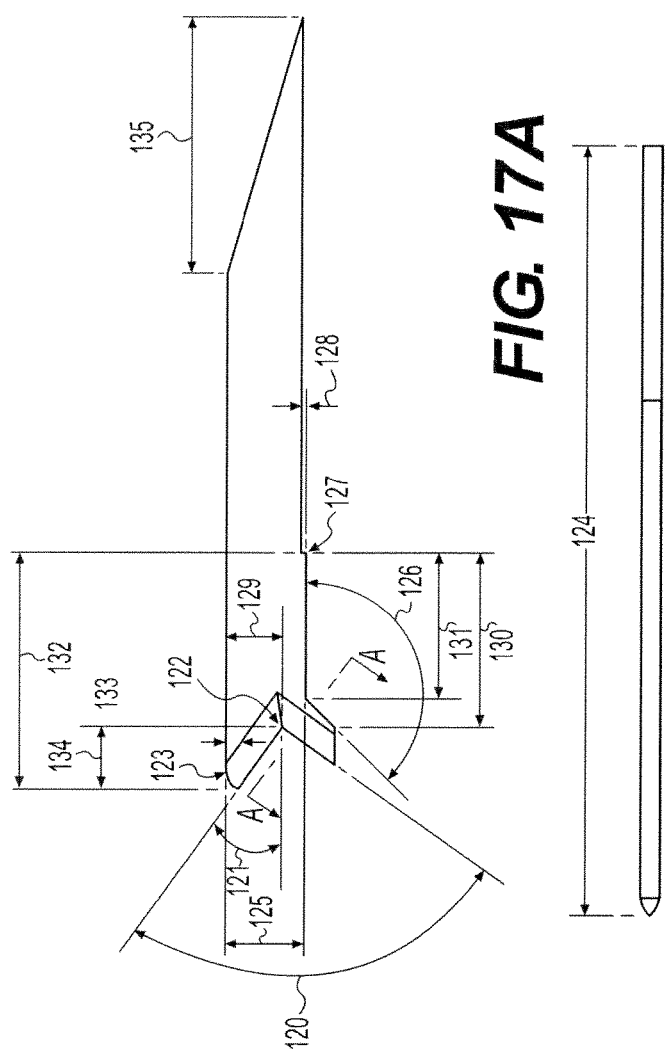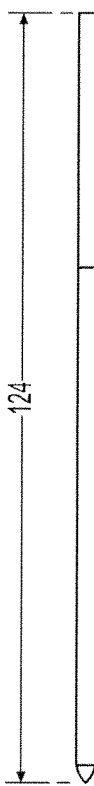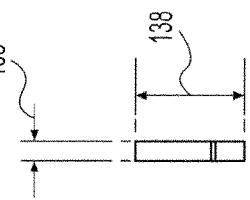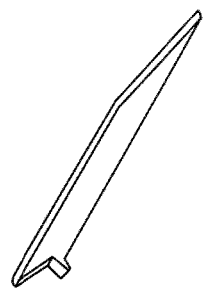
FIG. 17A
FIG. 17B
FIG. 17C
FIG. 17D
FIG. 17E

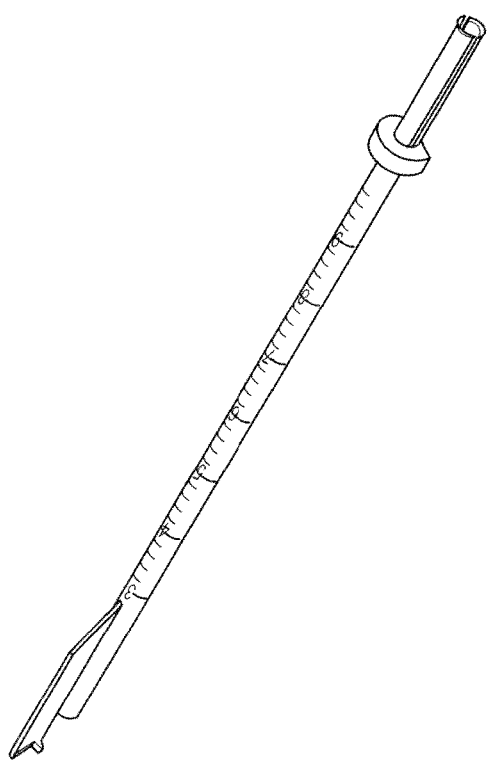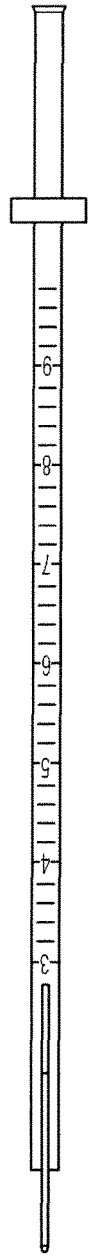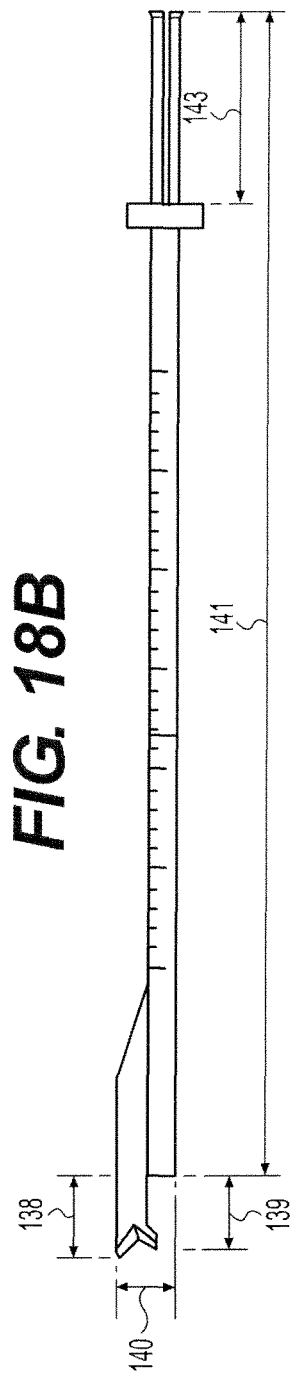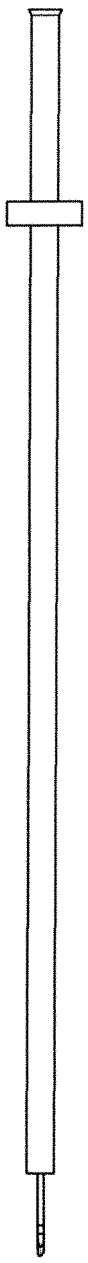
FIG. 18A
FIG. 18B
FIG. 18C
FIG. 18D

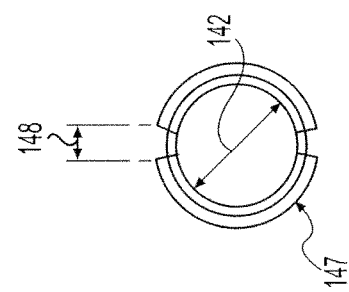
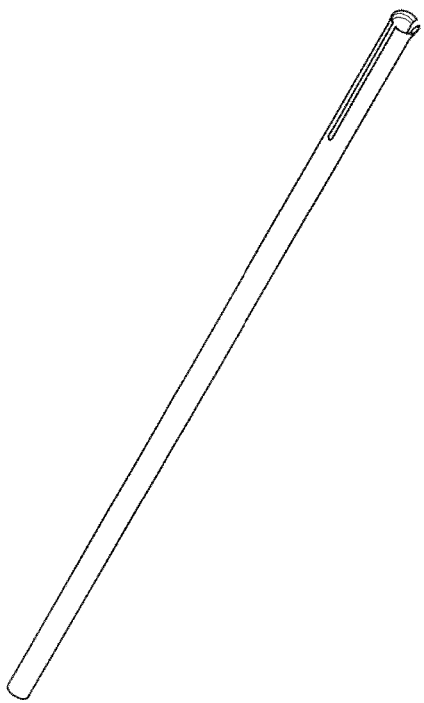
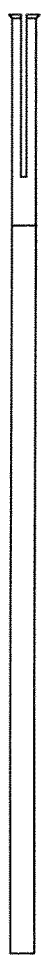
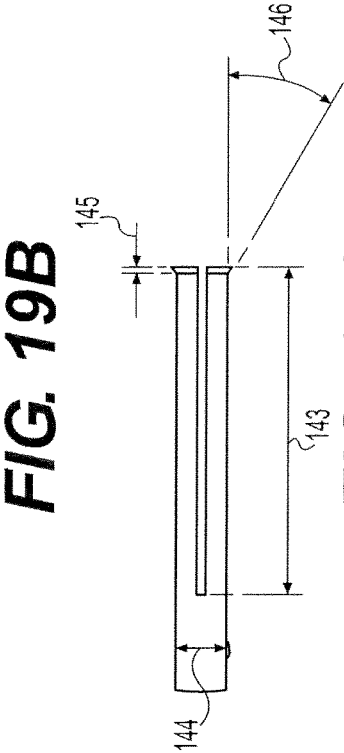

ENDOSCOPIC SURGICAL BLADE AND USE THEREOF

This application is a continuation-in-part application of U.S. patent application Ser. No. 12/716,640, filed on Mar. 3, 2010, which is a continuation-in-part application of U.S. patent application Ser. No. 12/400,485, filed on Mar. 9, 2009. The entirety of all of the aforementioned applications is incorporated herein by reference.

FIELD

The present invention relates to medical devices and, in particular, to a surgical blade for endoscopic operations.

BACKGROUND

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Among more recent developments and advances in endoscopic surgical procedures, arthroscopic surgery employing the use of endoscopic devices has found widespread application. For example, endoscopic procedures have been successfully used in effectuating carpal tunnel release with specially designed endoscopic instruments, such as those described in U.S. Pat. Nos. 5,366,465, 5,578,051, 5,968,061, and 7,041,115, all of which are incorporated herein by reference. However, there always exists a need to further improve the design of the instrument while reducing the cost.

SUMMARY

One aspect of the present invention relates to a blade for an endoscopic knife assembly, wherein the blade comprises an upper and a lower cutting surface on the forward edge of the blade, said cutting surfaces meeting at an angle at a crotch.

In one embodiment, the angle of the crotch is between about 80 degrees and about 100 degrees.

In another embodiment, the lower cutting surface extends below the main body of the blade.

In a further embodiment, the main body of the blade comprises a transition on the lower surface for mating the blade with a knife tube of an endoscopic knife assembly.

In another embodiment, the height of the blade as measured from the top edge to the transition is between about 1.5 mm and about 3.5 mm.

In another embodiment, the height of the blade as measured from the top edge to the transition is about 2.7 mm.

Another aspect of the present invention relates to an endoscopic knife assembly, comprising a blade, a knife tube and an alignment ring, wherein the assembly is insertable into a slotted cannula, wherein the blade comprises an upper and a lower cutting surface on the forward edge of the blade, said cutting surfaces meeting at an angle at a crotch.

In another embodiment, the combined height of the knife tube and blade is between about 4 mm and about 7 mm.

In another embodiment, the combined height of the knife tube and blade is about 5.817 mm.

In another embodiment, the posterior end of the knife tube is slotted for the attachment of a locking assembly to the knife tube and alignment ring.

Another aspect of the present invention relates to an instrument kit for implementing an endoscopic surgical procedure comprising, an endoscopic knife assembly and a slotted cannula for endoscopic surgical procedures, wherein said endoscopic knife assembly is insertable into the slotted cannula.

In another embodiment, the instrument kit further comprises an endoscope sized for insertion into the cannula and passing through the knife tube of the endoscopic blade assembly.

BRIEF DESCRIPTION OF THE DRAWINGS

The present invention can be better understood by reference to the following drawings. The drawings are merely exemplary to illustrate certain features that may be used singularly or in combination with other features and the present invention should not be limited to the embodiments shown.

FIG. 17A-E illustrate a blade component of an endoscopic knife assembly.

FIG. 18A-G illustrate an endoscopic knife assembly.

FIG. 19A-E illustrate the knife tube component of the endoscopic knife assembly.

DETAILED DESCRIPTION

Figure 1:
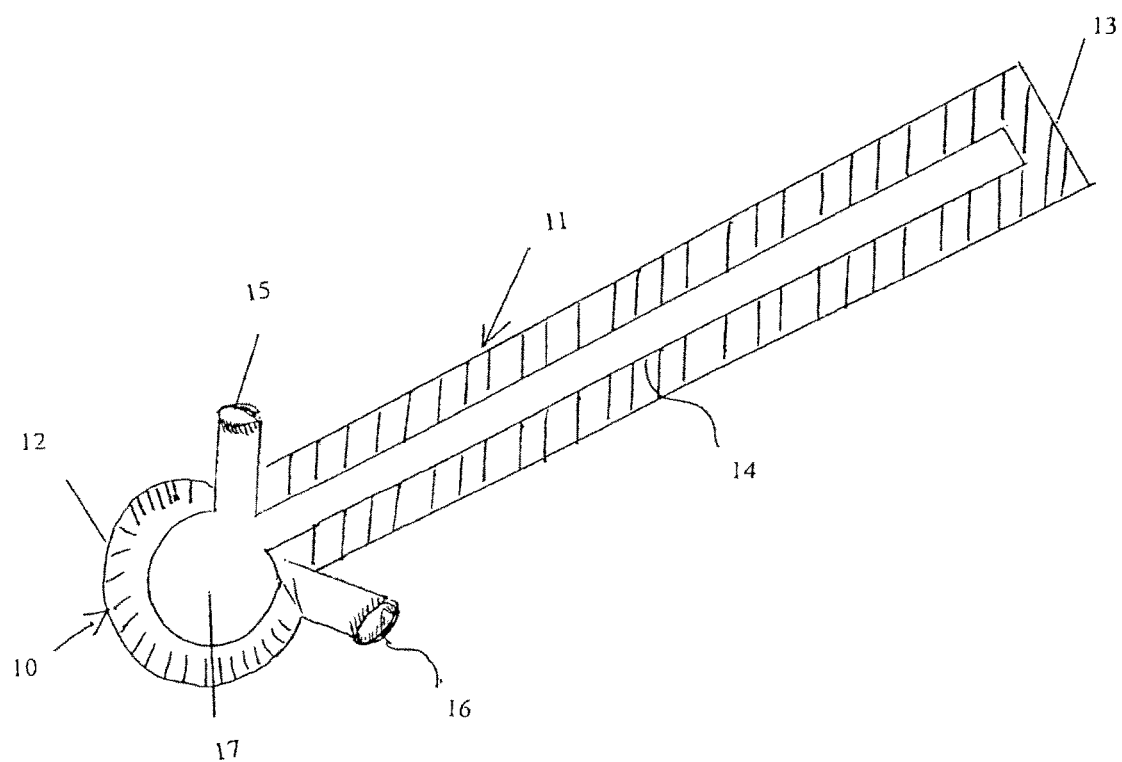
FIG. 1 illustrates a three-dimensional view of an embodiment of a slotted transparent cannula.

One aspect of the present invention relates to a slotted transparent cannula 10 (FIG. 1), specifically designed for endoscopic surgical procedures. The cannula 10 has a tubular body 11 with a proximate end 12 and a distal end 13, a slot 14 extending longitudinally from the beginning of the proximate end 12 to the proximity of the distal end 13, and a flange and a pair of wings 15 and 16 integrally formed on the proximate end 12. The slot 14 starts at the very beginning of the proximate end of the tubular body 11 so that an instrument with a matching structure, such as a protrusion, can be inserted into the cannula 10 from the proximate end of the tubular body. The slot 14 ends at a short distance from the distal end of the tubular body 11 to prevent excessive advancement of cannula mount surgical tools, such as obturators or blades at the surgical site. The tubular body 11 is made from a transparent material and has an inner diameter large enough for an endoscope to pass through. In one embodiment, the wings 15 and 16 are formed on the opposing edges of the slot 14 and extend radially from the tubular body 11.

Figure 2:
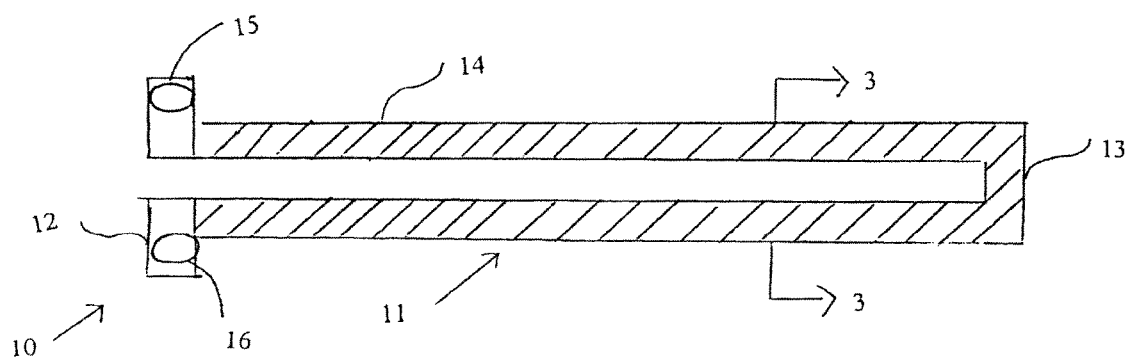
FIG. 2 illustrates a top view of the slotted transparent cannula.
Figure 3:
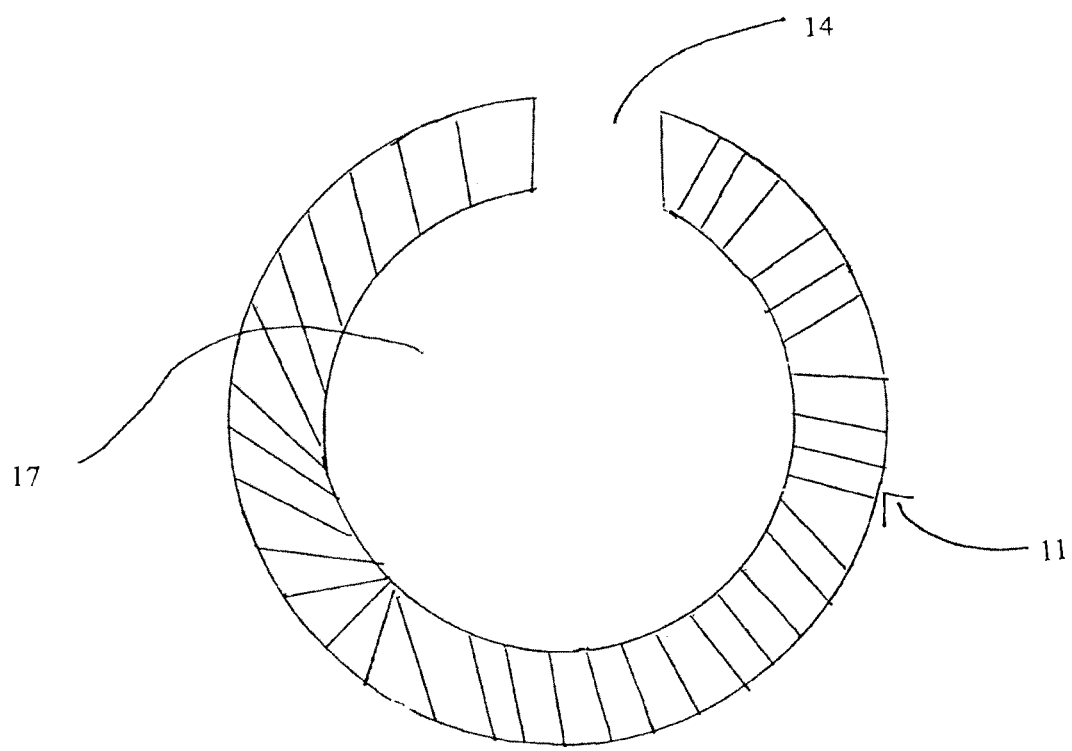
FIG. 3 illustrates a sectional view taken along line 3-3 in FIG. 2.

As shown in FIGS. 2 and 3, the tubular body 11 of the cannula 10 is circular in cross-sectional configuration and has a central aperture 17 to facilitate passage of an endoscope or other surgical devices. The central aperture 17 is sized to allow passage of the necessary surgical instruments, such as obturators and endoscopes, with sufficient clearance. In one embodiment, the central aperture has a diameter of 1-10 mm, preferably 2-8 mm, and more preferably 2-5 mm. While FIG. 2 shows a substantially circular central aperture 17, the central aperture can have a cross-section of any shape, so long as it allows the passage of an endoscope of other surgical devices. The outside diameter of the tubular body 11 varies with application but is typically in the range of 2-12 mm, preferably 4-10 mm, and more preferably 4-7 mm. The length of the tubular body 11 also varies with application. For example, the tubular body 11 would have a length of about 5-25 cm; preferably, 12-18 cm; and more preferably, 10-15 cm for carpal tunnel release and cubital tunnel release. The slot 14 allows a controlled movement of a passage of a surgical blade through the central aperture 17. In one embodiment, the slot 14 has a width in the range of 1-6 mm, preferably 1.5-5 mm, and more preferably 2-4 mm.

The wings 15 and 16 are integral parts of the tubular body 11 and extend outward radially to provide holding points for the cannula 10. In other embodiments, the wings 15 and 16 may be replaced with integrally formed outwardly extending curvilinear flange portions. In one embodiment, the flange portions are curved to match the curvature of the proximate end of an obturator. In another embodiment, the distal end of the cannula 10 may also be configured to form an integral obturator and dissector, thereby eliminating separate components.

In one embodiment, the cannula 10 is made from a transparent plastic material. As used hereinafter, the term "transparent plastic material" refers to a polymer material that has a light transmission rate equal to, or greater than, 80%. Preferably, the transparent plastic material has a light transmission rate equal to, or greater than, 90%.

The transparency of the cannula wall makes it possible to observe the anatomical structure around the insertion path with an endoscope. In addition, the plastic cannula is lightweight and can be made by injection molding to reduce cost. The transparent plastics used in the present invention should have good impact resistance and abrasion resistance. In one embodiment, the transparent plastics may be coated with a cover layer such as alumina or diamond like carbon, to improve abrasion resistance. The tubular body may further contain observation holes for better identification of the surrounding tissue. In one embodiment, the observation holes are oblong openings on the opposite side of slot 14.

Examples of transparent plastics include, but are not limited to, polyacrylate such as polymethlamethacrylate, polycarbonate, polystyrene, glycol modified polyethylene terephthalate, and cellulose acetate butyrate. Transparent plastics are commercially available under the trade names of Acrystex®, NAS®, Empera®, Kibiton®, Zylar®, Zytel®, etc.). The transparent cannula 10 can be used in combination with a variety of surgical instruments. Although these instruments have been shown in the Mirza U.S. Pat. Nos. 5,366,465, 5,578,051, 5,968,061 and 7,041,115, some of these instruments are described in detail herein for purposes of clarity the utility of the transparent cannula 10 of the present invention.

Figure 4:
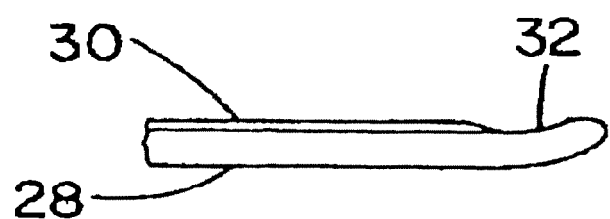
FIG. 4 illustrates a longitudinal side view of the leading end of an obturator adapted to be inserted into the slotted cannula of FIG. 1.
Figure 5:
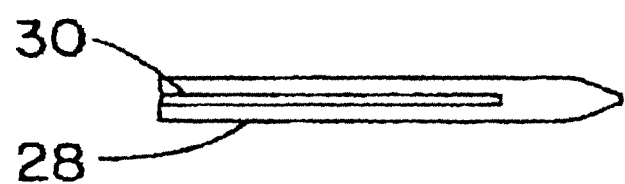
FIG. 5 illustrates a top view of the leading end of the obturator.

FIGS. 4 and 5 show an obturator 28 that is adapted to be slidably received within the cannula body 11, and presents a smooth outer surface through the intermediary of an axial, upstanding rib portion 30 which is engageable in close conformance within the longitudinal slot 14 of the cannula upon insertion therein. The distal end of the obturator 28 is a tapered tip portion 32 which is bent upwardly in a direction towards the longitudinal rib to impart to the tip a somewhat upward curvature.

Figure 6:
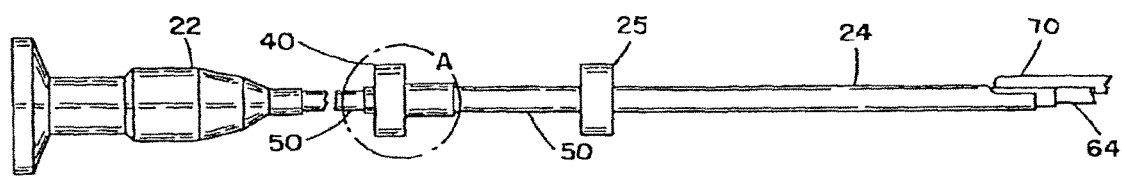
FIG. 6 illustrates a longitudinal side view of the endoscopic instrument, showing the scope and cutting device mounted on the latter inserted into the slotted cannula.
Figure 7:
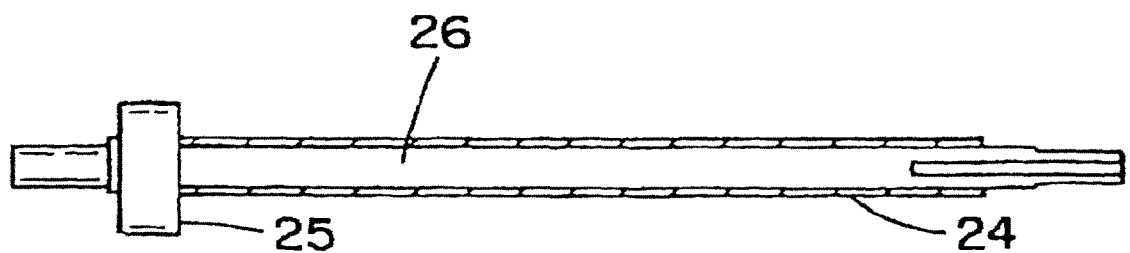
FIG. 7 illustrates a top view of the leading section of the endoscopic instrument shown in FIG. 6.
Figure 8:
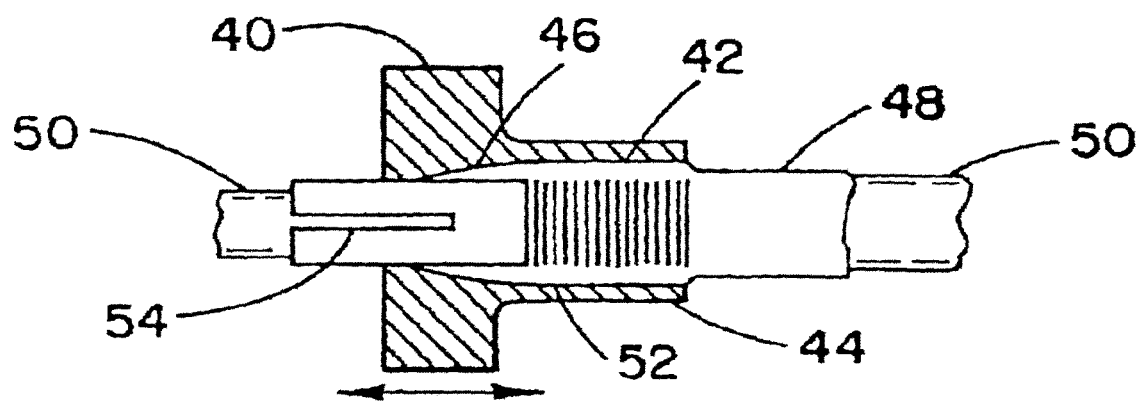
FIG. 8 illustrates, on a somewhat enlarged scale, a sectional view of the encircled portion A of the instrument of FIG. 6.
Figure 9:
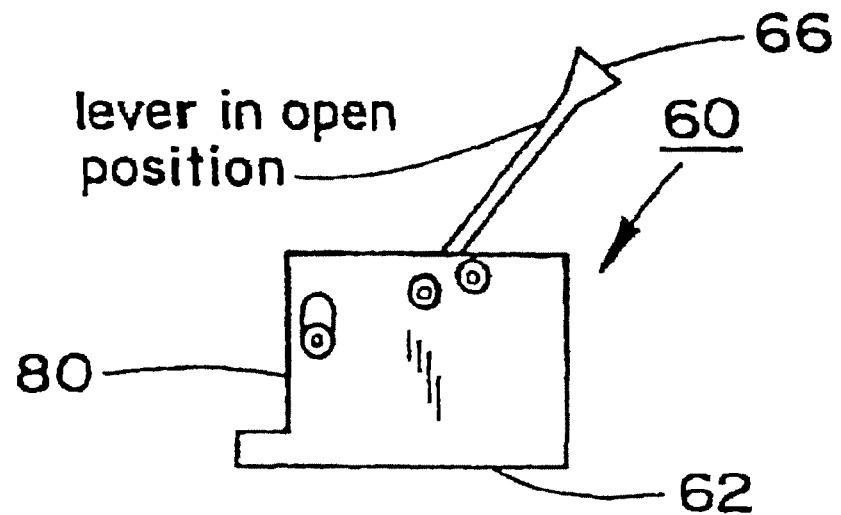
FIG. 9 illustrates a side view of the locking device.

FIGS. 6-8 show an arthroscope 22 that is adapted to be slidably received within the cannula 10. The arthroscope 22 includes a suitable knurled knob 40 having an internal threaded portion 42 in a cylindrical extension 44 and a tapered bore 46 for receiving a tubular knife or cutting blade holder 48. The blade or knife holder 48 is adapted to receive a scope 50 of cylindrical configuration extending therethrough and lock the latter within the blade holder by simply axially displacing the knurled nut 40 through threaded interengagement between the internal thread 42 of the nut and an external thread 52 on the blade holder. This will cause the tapered bore 46 of nut 40 to either compress the slotted portion 54 of the blade holder to clampingly engage the scope 50 or to loosen it so as to enable axial adjustment thereof relative to the blade holder A regular rod-like endoscope without a blade holder may also be inserted through the cannula for effective visualization of the operative site.

FIGS. 9-12 show a locking device 60 that can be used to lock the blade holder and the transparent cannula 10 into mutually fixed positions. The locking device 60 includes a rectangular housing structure 62 with a longitudinal through bore 64 for receiving a tubular element supporting a gauge or cutting blade and for receiving a rod like endoscope. A pivotable lever 66 mounted on the housing structure 62 is adapted to be swung between an opened position to a locked position so as to impart a clamping action to a tubular element extending through bore 64 by means of a camming structure.

Figure 10:
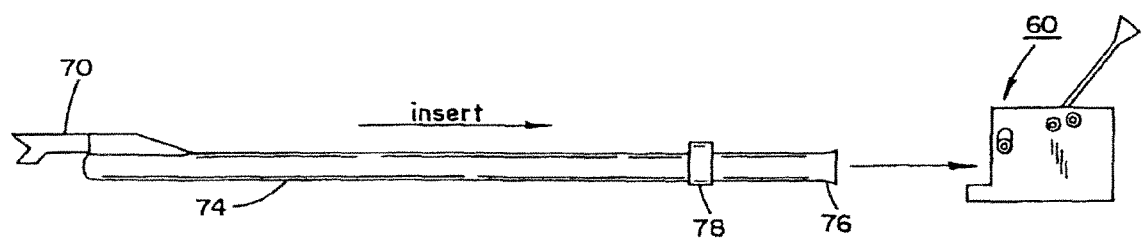
FIG. 10 illustrates a tubular member mounting a surgical knife being inserted into the locking device.

In one aspect, a cutting instrument, such as a surgical knife 70, which may be disposable, as shown in FIG. 10, is mounted at the leading end 72 of an elongate hollow tubular member 74 towards the opposite end of which the latter includes a hub portion 76 and a ring 78 spaced at a short distance therefrom, which forms a spacer defining the length of the tubular member 74 extending towards the knife blade 70, or any cutting or rasp instrument for removing tissue, such as a "curtain" of tissue, which is provided instead of the knife blade 70.

Figure 11:
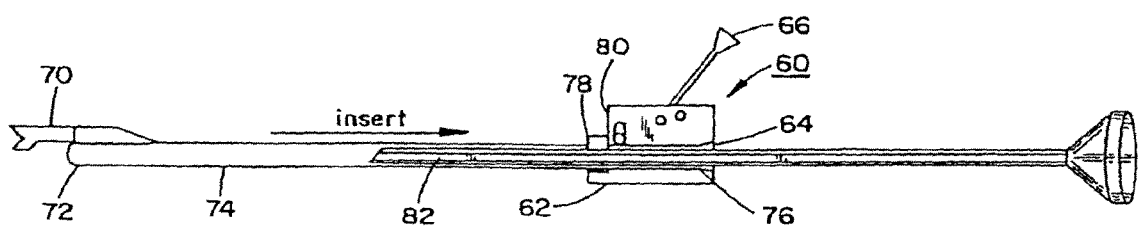
FIG. 11 illustrates the assembling of the components including an endoscope.
Figure 12:
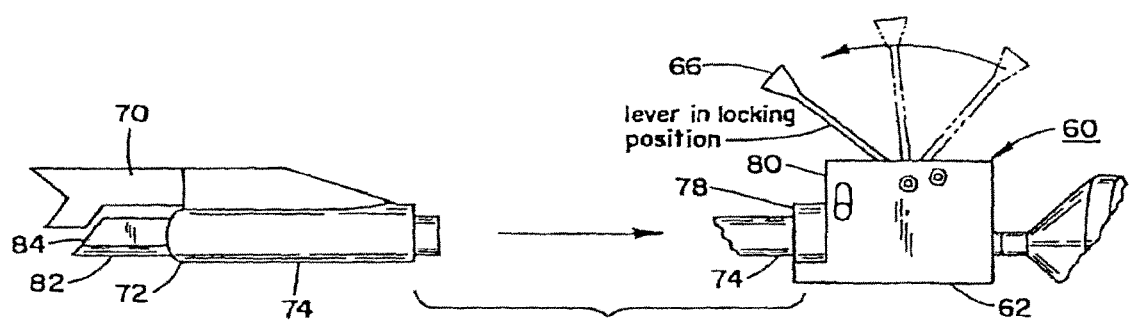
FIG. 12 also illustrates the assembling of the components including an endoscope.

As shown in FIGS. 10-12, in diagrammatic sequence, the hub end portion 76 of the hollow tubular member mounting the cutting or rasp instrument or the knife 70 at the opposite end 72 is adapted to be positioned within the bore 64 formed in the locking device 60, and is inserted therein to the extent such that the spacer 78 ring which is fastened to the tubular member 74 comes into contact with the leading or forward surface 80 of the locking device 70. At that point in time, the endoscope 82 is advanced through the hollow tubular member 74 which mounts the cutting instrument or knife 70, as shown in FIG. 11, and the leading end 84 of the endoscope 82 positioned closely to the cutting blade or instrument 70, similar to the arrangements described in the above-mentioned U.S. Pat. Nos. 5,366,465 and 5,578,051 to Mirza.

As shown in FIG. 12, as the endoscope 82 has its leading end 84 appropriately positioned in proximity relative to the knife or cutting instrument 70, the lever 66 is pivoted forwardly into the locking position, thereby causing the endoscope 82 to be clamped to the tubular member 74 mounting the cutting element or blade 70. This will then facilitate ready insertion of the resultingly locked together components into the slotted cannula 10.

Figure 13:
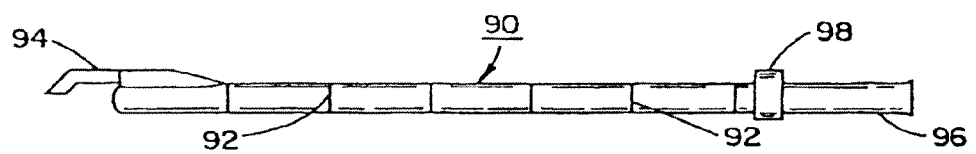
FIG. 13 illustrates the tubular member mounting a depth gauge.

The elongate tubular element 74, which mounts the knife or cutting element 70 at the leading end 72, may be calibrated along the length thereof so as to provide indication as to the depth to which the instrument is being introduced into the patient towards the surgical site. In this connection, in lieu of the tubular member mounting a knife or cutting element 70, prior to the use thereof with the endoscope 82, a tubular element 90 having calibrating markings 92 along the length thereof, which is similar to tubular element 74, may be equipped with a depth gauge 94 at the leading end thereof, as shown in FIG. 13, which, in a manner similar to the tubular member 74 mounting a knife or cutting element, is adapted to be inserted at the hub end 96 thereof into the locking device 60 until ring 98 contacts the locking device, with the endoscopic element inserted therein to provide illumination of the operating site, and the lever 66 being swung forwardly into the locking position.

Figure 14:
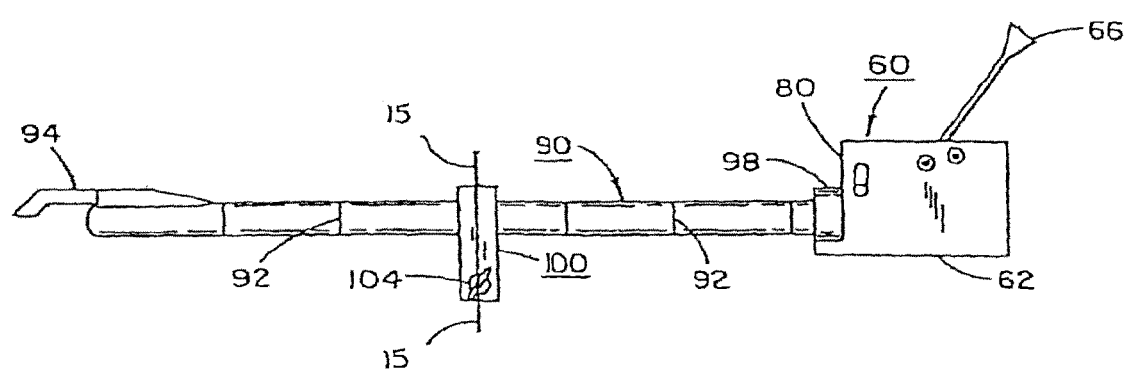
FIG. 14 illustrates the tubular member mounting the depth gauge connected to the locking device and having a stop device for limiting the extent of insertion into an incision formed in a patient.
Figure 15:
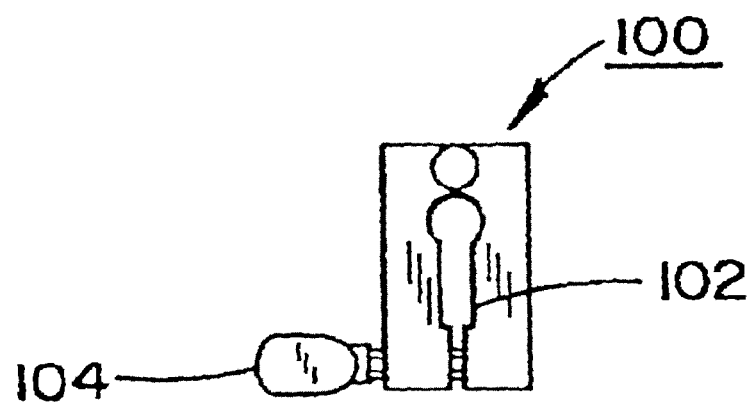
FIG. 15 is a sectional view taken along line 15-15 in FIG. 14.

Upon determination of the appropriate insertion depth to the surgical site by means of the tubular member 90 mounting the depth gauge 94, having the endoscope mounted therein, it is desirable to mount a stop device 100 in the form of a clamp member 102 on the tubular element 90 mounting the depth gauge 94, as shown in FIGS. 14 and 15, and tighten a clamping element 104, such as, for instance, a tightening screw, and which will provide information with regard to the cutting depth which is to be subsequently implemented, in that the stop device is positioned against or in proximity with the skin of the patient at the location of the incision, while the tubular element 90 and the endoscope therein are advanced within the cannula 10.

Upon withdrawing the tubular element 90 mounting the depth gauge 94 from the slotted cannula 10, a tubular element 74 mounting a knife or cutting instrument may be substituted therefore, as shown in the drawing FIGS. 10 to 12, and wherein the tubular member 74 or element mounting the knife or cutting instrument is similarly calibrated along its length. A stop device 100 is then fastened thereon at a location conforming with that of the stop device 100 which was previously mounted on the calibrated tubular member 90 mounting the depth gauge 94. This will enable the precise determination of the depth to which the cutting instrument can be inserted through the cannula 10 into the operating site, thereby preventing any injury due to any excessive penetration past the surgical site by the cutting instrument.

Figure 16:
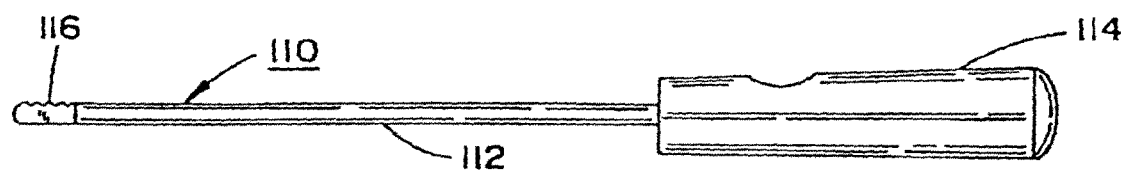
FIG. 16 illustrates a rasp member adapted to scrape a curtain of tissue at an operating site.

Furthermore, in lieu of the use of a knife blade being mounted on a tubular member 74, as the cutting element there may also be employed a unique rasp member 110 having a plurality of transverse cutting edges formed thereon, and which is adapted to scrape tissue at the operating site. The rasp member 110, as shown in FIG. 16, may be in the form of a solid rod element 112, which is insertable into the cannula 10, including a gripping end 114 and having the rasp elements 116 at the leading end thereof for advance towards the operating site. Alternatively, the rasp may comprise rasp elements mounted on a hollow tubular element similar of the type which supports the depth gauge 94 or knife 70, and is adapted to be fastened to the locking device 60 and with an endoscope passed therethrough, with the lever 66 of the locking device thereafter locking the components into mutually fixed positions.

The slotted transparent cannula and the endoscopic instruments described above may be readily applied surgical procedures such as carpal tunnel release; cubital tunnel release, plantar fascia release, lateral release for patella realignment, release of radial tunnel, release of pronatar teres, release of trigger finger, release of lacertous fibrosis, release of the extensor tendons for lateral epicondylitis (tennis elbow), release of medial epicondylitis (golfer's elbow), and release of fascial compartments in the upper and lower extremity. It is also possible to customize the slotted transparent cannula to adapt to other endoscopic surgical instrument for other endoscopic surgical procedures.

Another aspect of the present invention relates to an instrument kit for implementing an endoscopic surgical procedure. The instrument kit contains a transparent cannula guide member including a longitudinal bore having open proximal and distal ends and an open slot extending along the length thereof communicating with the open ends, and an elongate insertion member that is slidably receivable within the cannula guide member and is configured so that at least portions thereof conform with the open distal end and the open slot of the guide member to form a smooth exterior surface in combination therewith.

In one embodiment, the instrument kit further includes an endoscope sized for insertion into the cannula guide member for direct visualization of an operative site.

In another embodiment, the endoscope is capable to carry a cutting instrument at a leading end.

In another embodiment, the instrument kit further includes a cutting instrument mountable to the leading end of the endoscope.

In another embodiment, the instrument kit further includes a second endoscope with a cutting instrument mounted at a leading end of the second endoscope. The second endoscope is insertable into the cannula guide member such that the cutting instrument protrudes through the open slot in the cannula guide member.

In another embodiment, the instrument kit further includes a depth gauge mountable to a leading end of the endoscope.

In another embodiment, the instrument kit further includes a rasp member sized for insertion into the cannula guide member.

In another embodiment, the instrument kit further includes a locking device capable of locking the endoscope and the cannula guide member into mutually fixed positions.

In another embodiment, the instrument kit further includes a stop device mountable on the cannula guide member to prevent excessive penetration at a surgical site by the cutting instrument.

In another embodiment, the instrument kit further includes a curved dissector.

Another aspect of the present invention relates to a method for implementing a uniportal endoscopic surgical procedure using the slotted transparent cannula of the present invention. In one embodiment, the method includes the steps of making an incision on a patient in need of such endoscopic surgical procedure at a location proximate an operation site to establish an entry portal, inserting an elongate insertion member into a longitudinal bore of an elongate transparent cannula having open proximal and distal ends and an open slot extending along the length of the transparent cannula, the elongate insertion member being configured to form a smooth exterior surface at the open distal end of the transparent cannula when fully inserted into the transparent cannula; introducing the distal end of the transparent cannula/insertion member combination into the entry portal and advancing the combination a predetermined distance relative to the operation site; withdrawing the insertion member while permitting the transparent cannula to remain in place at the operation site; inserting a first endoscope into the transparent cannula for direct visualization of anatomic structures surrounding the transparent cannula and positioning of the transparent cannula at the operative site; withdrawing the first endoscope from the transparent cannula; mounting a cutting instrument on a leading end of a second endoscope; inserting the second endoscope with the cutting instrument into the transparent cannula such that the cutting instrument protrudes into the open slot in the transparent cannula, and advancing the second endoscope so that the cutting instrument is in contact with a target tissue at the operation site; operatively engaging the target tissue with the cutting instrument while advancing the latter under direct visualization through the second endoscope so as to perform a desired operative procedure on the target tissue; withdrawing the second endoscope and the cutting instrument from the transparent cannula; withdrawing the transparent cannula through the entry portal; and suturing the incision.

In one embodiment, the first endoscope and the second endoscope are the same endoscope. In another embodiment, the first endoscope and the second endoscope are different endoscopes.

The transparent cannula of the present invention can be inserted into the tissue through a small opening and advanced to a surgical site, thus forming a passageway towards the surgical site. The passageway allows the insertion of the endoscope and other instruments to the surgical site without further damages to the surrounding tissues. The transparent cannula body also allows endoscopic examination of the surrounding anatomical structures without any movement of the cannula body. The longitudinal slot provides improved visualization of the target anatomical structure and control over the inserted devices. The cannula is lightweight and can be produced at low cost. The slotted transparent cannula can be used in endoscopic surgical procedures such as carpal tunnel release, cubital tunnel release, plantar fascia release, lateral release for patella realignment, release of the extensor tendons for lateral epicondylitis (tennis elbow), release of the posterior and other compartments of the leg, and the forearm fascial release for fascial compartment syndrome.

Another aspect of the present invention is a scope-mounting blade or endoscopic knife assembly for endoscopic surgery. The knife assembly comprises a blade, a knife tube and an alignment ring. The assembly is assembled by affixing the alignment ring and the blade onto the knife tube.

In one embodiment, the blade is made from 440 A stainless steel, Rc 58 MIN. In a preferred embodiment, the blade is made from Hitachi GIN-5 SST-MODIFIED 440-A stainless steel. The blade is optionally flash electropolished. The cutting edges are machine finished and must be sharp.

FIG. 17A depicts a side view of the blade component of the endoscopic knife assembly, showing the cutting surfaces at the leading end of the blade, the transition where the blade is joined to the knife tube and the taper at the trailing end of the blade.

FIG. 17B is a perspective view showing a top view of the blade.

FIG. 17C is a perspective view showing the blade component at an angle.

FIG. 17D is an exploded view depicting an exemplary angle of a cutting surface of the blade component.

FIG. 17E is a perspective view of the blade from the back depicting the width of the blade, the transition and the extension of the lower cutting surface below the transition.

In a particular embodiment, the blade as shown in FIGS. 17A-E comprises upper and lower cutting surfaces on the leading end of the blade, which are at an angle 120 to one another and meet at a central crotch 122. In one embodiment the angle 120 is between about 80 and about 100 degrees. In a preferred embodiment, the angle 120 is between about 85 and about 95 degrees. In a more preferred embodiment, the angle 120 is about 90 degrees.

In some embodiments, the grinding of the upper and lower cutting surfaces where they meet at the crotch 122 has a maximum radius of about 0.65 mm. In a preferred embodiment, the crotch 122 has a maximum radius of about 0.5 mm. In a more preferred embodiment, the crotch 122 has a maximum radius of 0.381 mm. In some embodiments, the vertical distance 129 between the crotch and the upper edge of the blade is between about 1.5 mm and 2.5 mm. In a preferred embodiment, the vertical distance 129 is about 2.032 mm.

In a particular embodiment, the upper cutting surface is at an angle 121 to an imaginary line running through the crotch that is parallel to the knife tube. In one embodiment the angle 121 is between about 80 and about 100 degrees. In a preferred embodiment, the angle 121 is between about 85 and about 95 degrees. In a more preferred embodiment, the angle 121 is about 90 degrees. In another embodiment, the angle 121 is about 36 degrees.

In some embodiments, the end of the upper cutting surface distal to the crotch is also radiused 123. The radiused end 123 of the upper cutting surface is about 90 degrees of a circle and has a radius measurement between about 0.75 mm and 0.5 mm. In a preferred embodiment, the radius is about 0.635 mm.

In a preferred embodiment, the total length 124 of the blade from the leading point of the upper cutting surface to the trailing end of the blade is between about 15 mm and about 40 mm. In another preferred embodiment, the total length 124 of the blade from the leading point of the upper cutting surface to the trailing end of the blade is between about 26.72 mm and about 27.23 mm. In a more preferred embodiment the total length 124 of the blade is about 26.97+/−0.254 mm.

In a particular embodiment, the height 125 of the main body of the blade is between about 2 mm and about 3.5 mm. In another embodiment, the height 125 of the main body of the blade is between about 2.54 mm and about 3.048 mm. In a preferred embodiment, the height 125 of the main body of the blade is between about 2.667 mm and about 2.921 mm. In a more preferred embodiment, the height 125 of the main body of the blade is about 2.794 mm.

In another embodiment, as shown in FIGS. 17A, C & E, the lower cutting surface extends below the height 125 of the main body of the blade. In one preferred embodiment, the lower cutting surface extends below the height 125 of the main body of the blade from about 0.5 mm to about 1.5 mm. In another preferred embodiment, the lower cutting surface extends below the height 125 of the main body of the blade from about 0.762 mm to about 1.27 mm. In a more preferred embodiment, the lower cutting surface extends below the height 125 of the main body of the blade about 1.016 mm. Accordingly, in a preferred embodiment, the vertical height 138 of the blade from the top surface of the main blade to the bottom of the lower cutting surface is between about 2.5 mm to about 5 mm, or about 3.810 mm in a more preferred embodiment. The angle 126 at which this extension of the lower cutting surface meets the main body of the blade is preferably between about 125 degrees and about 145 degrees. In a preferred embodiment, the angle 126 at which this extension of the lower cutting surface meets the main body of the blade is between about 130 degrees and about 140 degrees. In a more preferred embodiment, the angle 126 at which this extension of the lower cutting surface meets the main body of the blade is about 135 degrees.

In order to insure that, during manufacture, the blade is consistently joined to the knife tube in the same location, the lower surface of the main body of the blade comprises a transition 127. During assembly of the endoscopic knife assembly, the notch of the transition 127 is butted against the front of the knife tube. Following the positioning of the blade on the knife tube, the blade is laser welded all around to the knife tube. In a particular embodiment, the strength of the weld is tested by applying torque to the unit, for example about 10 in-lbs of torque. In a first embodiment, the depth 128 of the notch of the transition is preferably between about 0.025 mm and about 0.18 mm. In a preferred embodiment, the depth 128 of the notch of the transition is preferably between about 0.051 mm and about 0.1524 mm. In a more preferred embodiment, the depth 128 of the notch of the transition is about 0.102 mm. Additionally, in a preferred embodiment, the height of the blade from the top of the transition notch to the top edge of the blade is between about 1.5 mm and about 3.5 mm, more preferably about 2.7 mm.

In order to maintain uniform measurement of the gradations on the knife tube and the cutting surfaces of the blade, the horizontal distance 130 between the transition 127 and the crotch 122 of the blade is preferably 6.096 mm. Alternatively, a horizontal distance 130 can be chosen for a particular model or lot of the blade within a range of about 4 mm to about 10 mm. The horizontal distance 131 between the transition 127 and the angle 126 at which the lower cutting surface extends from the main body of the blade is preferably 5.08 mm. The horizontal distance 132 between the transition 127 and the beginning of the radius 123 at the leading edge of the upper cutting surface is within the range of 5 mm to about 10 mm, preferably about 7.57 mm to about 7.67 mm, and more preferably about 7.62 mm. The vertical distance 133 between the top of the blade and the forward edge of the radius 123 is preferably about 0.585 to about 0.685, and more preferably about 0.635 mm. The horizontal distance 134 between the forward edge of the radius 123 and the crotch 122 is preferably about between about 1.7 mm and about 2.5 mm, and more preferably about 2.134 mm.

In order to prevent the blade from catching on the interior surface of the cannula when the blade is drawn backwards through the cannula tube, the trailing edge of the blade is tapered 135 down to the knife tube. In a preferred embodiment, the horizontal length of the taper 135 is between about 5 mm to about 15 mm, preferably about 8.89 mm to about 9.04 mm. In a more preferred embodiment, the horizontal length of the taper 135 is about 8.97 mm.

In a particular embodiment, the width 136 of the blade is between about 0.4 mm and about 0.7 mm, preferably between about 0.62 mm and about 0.65 mm. In a more preferred embodiment, the width 136 of the blade is about 0.635 mm.

In a further preferred embodiment, the angle 137 of the cutting surface is between about 35 degrees and about 45 degrees. In a yet further preferred embodiment, the angle 137 is between about 37.5 degrees and about 42.5 degrees. In a more preferred embodiment, the angle 137 is about 40 degrees.

The blade is mounted to the knife tube as shown in FIG. 18A-G.

FIG. 18A is a perspective view of the endoscopic knife assembly from an angle.

FIG. 18B is a perspective view of the endoscopic knife assembly from the top.

FIG. 18C is a perspective view of the endoscopic knife assembly from the side.

FIG. 18D is a perspective view of the endoscopic knife assembly from the bottom.

Figure 18G:
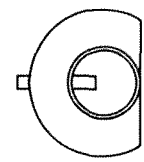
Figure 18F:
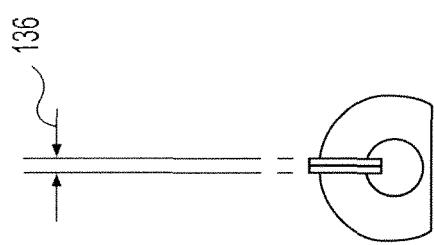
Figure 18E:
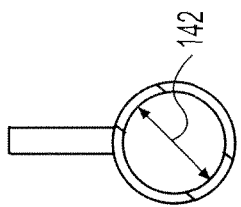

FIG. 18E is a perspective view of the endoscopic knife assembly from the back as a cross-section forward of the alignment ring, posterior to the blade.

FIG. 18F is a perspective view of the endoscopic knife assembly from the front.

FIG. 18G is a perspective view of the endoscopic knife assembly from the rear.

FIGS. 18A & C, in particular, show the blade component of FIGS. 17A-E welded to the knife tube such that the notch of the transition is butted up against the front of the knife tube.

In a particular embodiment, the leading point of the upper cutting surface extends a distance 138 of about 5 mm to about 12 mm, preferably about 7.976 mm to about 8.611 mm forward of the knife tube. In a more preferred embodiment, the distance 138 is about 8.23 mm.

In another preferred embodiment, the leading point of the lower cutting surface extends a distance 139 of about 4 mm to about 11 mm, more preferably about 7.391 mm forward of the knife tube.

In a particular embodiment, the distance 140 from the top edge of the blade to the underside of the knife tube is a distance of between about 4 mm to about 7 mm. In a preferred embodiment, the distance 140 from the top edge of the blade to the underside of the knife tube is a distance of between about 5.309 mm to about 6.325 mm. In another preferred embodiment, the distance 140 is between about 5.563 mm to about 6.071 mm. In a more preferred embodiment, the distance 140 is about 5.817 mm.

In a particular embodiment, the length 141 of the knife tube is from about 100 mm to about 140 mm, preferably from about 114.3 mm to about 119.4 mm. In a more preferred embodiment, the length 141 of the knife tube is about 116.8 mm.

The inner diameter 142 of the knife tube is such that an endoscope camera can be inserted into the knife tube in order to show the blade and the target tissue during a procedure. In one embodiment, the inner diameter 142 is between about 2 mm and about 3.5 mm. In a preferred embodiment, the inner diameter 142 is between about 2.769 mm and about 2.87 mm. In a more preferred embodiment, the inner diameter 142 is about 2.819 mm.

The knife tube can optionally be marked on the top or side surface with gradations as exemplified in FIGS. 18A and 18B to show the distance to the crotch of the cutting surfaces. For example, major gradations can be made to show each centimeter in distance from the crotch, with minor gradations between them to show each 1, 2, 2.5 or 5 millimeters. While the gradations can be applied to the knife tube by any means known in the art, it is preferable to lasermark the gradations on the knife tube for accuracy and permanence. Additionally, the knife tube can also be marked in a similar manner with additional information, for example on the bottom or a side surface of the knife tube. Exemplary markings may include, but are not limited to, a maker's mark, part number, lot number and an indication that the endoscopic knife assembly is intended for only a single use.

The alignment ring is affixed near the posterior end of the knife tube. During assembly, the alignment ring is affixed in position on the knife tube using USP Class VI gamma irradiation and steam resistant epoxy adhesive. Preferably, a two part epoxy such as MASTERBOND EP42 HT or ARMSTRONG C-7, or a suitable equivalent thereof is used. In one embodiment, the distance 143 between the alignment ring and the posterior end of the knife tube is between about 15 mm and about 25 mm. In a preferred embodiment, the distance 143 between the alignment ring and the posterior end of the knife tube is between about 18.67 mm and about 19.43 mm. In a more preferred embodiment, the distance 143 is about 19.05 mm.

The knife tube further comprises slots in the posterior end that are positioned on the sides of the tube, perpendicular to the blade mounted on the top of the knife tube. The slots preferably extend forward to where the alignment ring is affixed to the knife tube.

The slots and alignment ring provide an attachment point for a locking device, in order to mount an endoscope to the scope-mounting blade or endoscopic knife assembly.

FIGS. 19A-E are perspective views of a knife tube without an affixed blade or alignment ring and without gradations.

FIG. 19A is a perspective view from the bottom of a knife tube, shown at an angle.

FIG. 19B is a perspective view from the side of a knife tube.

FIG. 19C is a magnified view from the side of the posterior end of a knife tube, showing the slots and the flared end.

FIG. 19D is a perspective view from the top or bottom of a knife tube.

FIG. 19E is a perspective view of the posterior end of a knife tube, showing the slots and the flared end.

In a particular embodiment, the outer diameter 144 of the knife tube is between about 2.8 mm and about 3.6 mm, preferably between about 3.073 mm and about 3.175 mm. In a more preferred embodiment, the outer diameter 144 is about 3.124 mm.

In another particular embodiment, the posterior end of the knife tube is flared 145. In particular, the about 0.2 to about 0.5 most posterior millimeters of the knife tube are flared. In a preferred embodiment, about the 0.381 most posterior millimeters of the knife tube are flared. In another preferred embodiment, the angle 146 of the flare is about 20 to 40 degrees, more preferably about 30 degrees. In still another preferred embodiment, the outer diameter 147 of the flared portion 145 of the knife tube is about 0.25 mm to about 0.45 mm, more preferably about 0.356 mm.

Preferably, the slots 143 are between about 0.4 mm and about 1.1 mm wide, more preferably between about 0.533 mm and about 0.914 mm wide 148. Even more preferably, the width 148 of the slots is about 0.6604 mm.

FIGS. 20A-D are perspective views of an exemplary alignment ring of the endoscopic knife assembly of the invention.

Figure 20B:
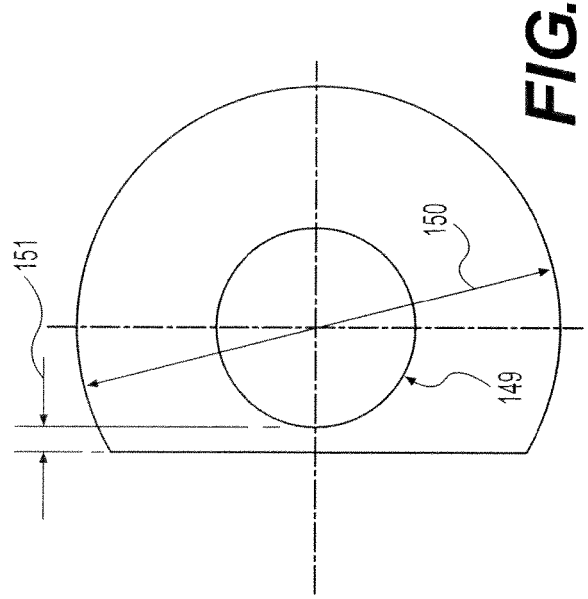
FIG. 20A-D illustrate the alignment ring component of the endoscopic knife assembly.
Figure 20D:
Figure 20A:
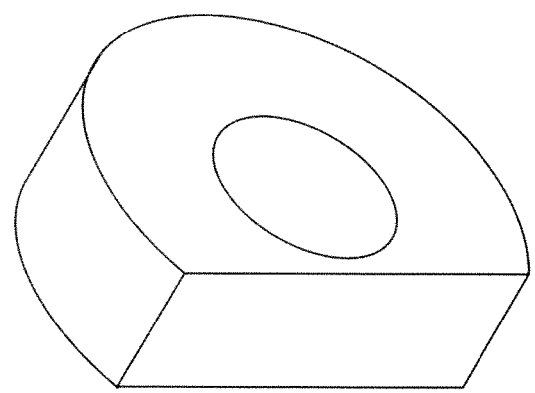

FIG. 20A is a perspective view at an angle as seen from the bottom, showing the flattened bottom face of the alignment ring.

FIG. 20B is a perspective view at an angle as seen from the front or back face of the alignment ring.

Figure 20C:
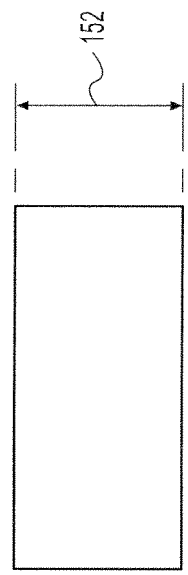

FIG. 20C is a perspective view seen from the side of the alignment ring.

FIG. 20D is a perspective view seen from the top of the alignment ring.

In a particular embodiment, the alignment ring has a flattened face that, when the alignment ring is affixed to the knife, is oriented on the bottom of the knife tube, i.e., opposite of the mounting of the blade. When the endoscopic knife assembly is fully assembled, the flat face of the alignment ring forms a right angle with the vertical orientation of the affixed blade, as depicted in FIGS. 18F and 18G.

In a particular embodiment, the inner diameter 149 of the alignment ring, which must fit on the outside of the knife tube, is between about 2.8 mm and about 3.7 mm, preferably between about 3.15 mm and about 3.175 mm. In a more preferred embodiment, the inner diameter 149 is about 3.15 mm.

In a further particular embodiment, the outer diameter 150 of the alignment ring is between about 6 mm and about 10 mm, preferably between about 7.569 mm and about 7.671 mm. In a more preferred embodiment, the outer diameter 150 is about 7.62 mm.

In another particular embodiment, the distance 151 between the inner opening 149 of the alignment ring and the flattened face, on a line perpendicular to the flattened face, is between about 0.25 mm and about 0.5 mm, preferably between about 0.330 mm and about 0.432 mm. In more preferred embodiment, the distance 151 is about 0.381 mm.

The present invention is further illustrated by the following examples which should not be construed as limiting. The contents of all references, patents and published patent applications cited throughout this application, as well as the Figures and Tables are incorporated herein by reference.

Example 1: Use of the Slotted Transparent Cannula (Hereinafter "Clear Cannula") for Endoscopic Carpal Tunnel Release 1-a. Preparation of the Clear Cannula Prepare the Clear Cannula for insertion by introducing the obturator through the cannula. The prong at the distal end of the obturator should be between the wings of the cannula. This ensures that the distal tip of the obturator is oriented correctly.

1-b. Introduction of Clear Cannula

A single incision is made in the palm proximate the distal side of the transverse carpal ligament (TCL). A curved dissector is inserted to form a passage beneath the TCL. Once the pathway is created and the dissector removed, the obturator and the Clear Cannula are introduced into the same pathway. The cannula tip should always stay against the under surface of the TCL and superficial to the flexor tendons and ulnar bursa. Prior to removal of the obturator rotate the assembly so the slot of the cannula faces slightly toward the ulnar side. The cannula should not be rotated past two and ten o'clock respectively.

1-c. Endoscopic Visualization of Anatomy

A 4 mm, 30 degree endoscope, oriented towards the slot of the cannula, is then introduced into the cannula Visualization of the transverse carpal ligament fibers and fibers of the antebrachial fascia should be visible through the slotted portion of the cannula. If the transverse fibers of the TCL are not clearly seen, the cannula must be removed using the obturator and the introduction procedure repeated.

The Clear Cannula should allow for adequate visualization of the median nerve and flexor tendons without the need to rotate the slot of the cannula towards these anatomic structures. Due to variations of anatomy, visual confirmation of these structures may not be possible. If visualization of these structures is inadequate, the surgeon may rotate the slot of the cannula towards the median nerve (radial) and flexor tendons (ulnar) to verify proper cannula placement.

1-d. Division of the Transverse Carpal Ligament

With a clear view of the transverse fibers of the TCL and no other intervening structures visible within the slotted portion of the cannula, the endoscope is removed from the cannula. The scope-mounting blade or endoscopic knife assembly is attached to the endoscope via the locking device.

The scope-mounting blade/scope assembly is introduced into the cannula and, as the surgeon observes the monitor, the TCL is divided by advancing the scope-mounted blade through the cannula in a proximal direction.

Once division is complete, remove the blade/scope assembly from the cannula, remove the blade from the endoscope and confirm division by reintroducing the endoscope into the cannula. Once division has been verified remove the Clear Cannula by reintroducing the obturator. The Clear Cannula should not be removed without first introducing the obturator).

This procedure dramatically reduces the risk of damaging any tissue and nerves, such as the median nerve, in the vicinity of the operating site. It also enables the surgeon to exercise an improved degree of control over the possibly single-handed manipulation of the endoscopic instrument and cutting blade.

Example 2: Use of the Clear Cannula for Endoscopic Cubital Tunnel Release 2-a. Preparation of the Clear Cannula Prepare the Clear Cannula for insertion by introducing the obturator through the cannula. The prong at the distal end of the obturator should be between the wings of the cannula. This ensures that the distal tip of the obturator is oriented correctly.

2-b. Introduction of the Clear Cannula

An "X" is placed on both the medial epicondyle and olecranon. A 3-4 cm incision is made along the course of the ulnar nerve at the cubital tunnel between the marked anatomical structures. A dissector is inserted to form a passage beneath the distal and proximal ulnar sheath. Once the distal or proximal pathway is created and the dissector removed, introduce the obturator and Clear Cannula into the same pathway. The surgeon should have direct visualization of the ulnar nerve so that the slotted portion of the cannula can be positioned 180 degrees to the ulnar nerve. Remove the obturator.

2-c. Endoscopic Visualization of Anatomy

A 4 mm, 30 degree endoscope, oriented towards the slot of the cannula, is then introduced into the cannula. Visualization of the (distal/proximal) ulnar nerve sheath should be visible through the slotted portion of the cannula. If the transverse fibers of the fascia are not clearly seen, the cannula must be removed using the obturator and the introduction procedure repeated.

The Clear Cannula should allow for adequate visualization of the ulnar nerve and surrounding tissue without the need to rotate the slot of the cannula towards these anatomic structures. Due to variations of anatomy, visual confirmation of the ulnar nerve may not be possible. If visualization is inadequate, the surgeon may rotate the slot of the cannula towards the ulnar nerve to verify proper cannula placement.

2-d. Division of the Distal and Proximal Ulnar Sheath

With a clear view of the transverse fibers of distal/proximal unar sheath and no other intervening structures visible within the slotted portion of the cannula, the endoscope is removed from the cannula. The scope-mounting blade or endoscopic knife assembly is attached to the endoscope via the locking device.

The scope-mounting blade/scope assembly is introduced into the cannula and, as the surgeon observes the monitor, the sheath is divided by advancing the scope-mounted blade through the cannula.

Once division is complete, remove the blade/scope assembly from the cannula, remove the blade from the endoscope and confirm division by reintroducing the endoscope into the cannula. Once division has been verified, remove the Clear Cannula by reintroducing the obturator. The Clear Cannula should not be removed without first introducing the obturator.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A blade for an endoscopic knife assembly, the endoscopic knife assembly comprising the blade and a tube, wherein the blade comprises: a distal blade portion, and a planar main body, wherein the blade comprises a notch formed within the blade, wherein at least a portion of a lower edge of the blade is in contact with an outer cylindrical surface of the tube, wherein the planar main body extends along an axis parallel to a longitudinal centerline of the tube of the endoscopic knife assembly, wherein the distal blade portion includes a radiused top edge facing away from the planar main body, and upper and lower beveled cutting edges radiating from a crotch at the distal blade portion, wherein the lower edge of the blade is on an opposite side of the blade from the radiused top edge of the distal blade portion, wherein the notch is formed on the lower edge of the blade so that: the notch formed within the blade is on the opposite side of the blade from the radiused top edge of the distal blade portion, and the notch engages a cylindrical surface of the tube, wherein the distal blade portion is distal from the notch.

2. The blade of claim 1, wherein the upper and lower beveled cutting edges radiate from one another at an angle between about 80 degrees and about 100 degrees.

3. The blade of claim 1, wherein the lower beveled cutting edge extends below the planar main body and wherein the height of the planar main body is between about 2 mm and about 3.5 mm.

4. The blade of claim 1, wherein the depth of the notch is between about 0.051 mm and about 0.1524 mm.

5. The blade of claim 1, wherein the planar main body of the blade comprises a tapered upper edge at the main body, and wherein the upper beveled cutting edge is radiused relative to an upper edge of the distal blade portion.

6. The blade of claim 1, wherein the upper and lower beveled edges are formed from cutting surfaces radiating from the planar main body at an angle between about 35 degrees and about 45 degrees.

7. The blade of claim 1, wherein a single trailing edge of the main body is tapered from an upper edge of the planar main body to where the main body contacts the tube, forming a tapered section with a horizontal length of between about 5 mm and about 15 mm.

8. The blade of claim 1, wherein an upper edge of the planar main body meets the upper beveled cutting edge at an opposite side of the blade relative to the lower edge of the planar main body where the notch is formed, and wherein the upper and lower edges of the planar main body define a longitudinal axis of the planar main body.

* * * * *